United States Patent [19]

Kleinschroth et al.

[11] Patent Number: 5,438,050

[45] Date of Patent: Aug. 1, 1995

[54] INDOLOCARBAZOLE DERIVATIVES, PROCESSES FOR THEIR PREPARATION AND COMPOSITIONS CONTAINING THEM

[75] Inventors: Jurgen Kleinschroth, Denzlingen; Johannes Hartenstein, Stegen-Wittental; Hubert Barth, Emmendingen; Christoph Schächtele, Freiburg; Claus Rudolph, Vorstetten; Gunter Weinheimer, Denzlingen; Hartmut Osswald, Tubingen, all of Germany

[73] Assignee: Gödecke Aktiengesellschaft, Berlin, Germany

[21] Appl. No.: 184,538

[22] Filed: Jan. 21, 1994

Related U.S. Application Data

[63] Continuation-in-part of Ser. No. 484,445, Feb. 20, 1990, abandoned, which is a continuation of Ser. No. 304,061, Jan. 30, 1989, abandoned, and Ser. No. 73,255, Jun. 7, 1993, abandoned, which is a continuation of Ser. No. 424,015, Oct. 19, 1989, abandoned.

[30] Foreign Application Priority Data

Feb. 6, 1988 [DE] Germany .................. 38 03 620.7
Oct. 21, 1988 [DE] Germany .................. 38 35 842.5

[51] Int. Cl.⁶ .................. A61K 31/40; A61K 31/495; C07D 241/36; C07D 245/04
[52] U.S. Cl. .................. 514/183; 514/219; 514/254; 540/472; 540/556; 544/339; 544/340; 548/417
[58] Field of Search .............. 548/416; 514/410, 183, 514/219, 254; 540/555, 471, 556, 472; 544/339, 340

[56] References Cited

U.S. PATENT DOCUMENTS 4,785,085 11/1988 Kaneko et al. .................. 536/23
4,808,613 2/1989 Kaneko et al. .................. 514/42
4,923,986 5/1990 Murakata et al. .................. 540/545

OTHER PUBLICATIONS

Biochemical and Biophyscial Research Communications, Mar. 13, 1986 vol. 135, No. 2, 1986 pp. 397–402, Tamaoki et al., "Staurosporine, a Potent Inhibitor of Phospholipid/Ca++ Dependent Protein Kinase".
Tetrahedron Letters, vol. 24, No. 13 pp. 1441–1444, (1983), Hughes et al. "Synthesis of Arcyriaflavin R".
The Journal of Organic Chemistry, vol. 52 No. 7, Apr. 3, 1987, Joyce et al., "Synthesis of the Aromatic and Monosaccharide Moieties of Staurosporine", pp. 1177–1185.
Chemical Abstracts, 107:236750y, p. 796, (1987) Hirata, et al.

Primary Examiner—Joseph Paul Brust
Attorney, Agent, or Firm—Elizabeth M. Anderson

[57] ABSTRACT

New indolocarbazoles of formula:

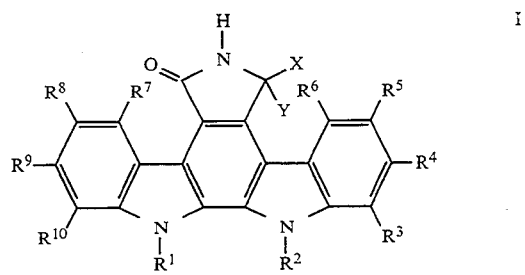

or a pharmaceutically acceptable salt thereof, processes for their preparation, compositions containing, and methods for using the composition for the inhibition of protein kinases, such as protein kinase C, for the prevention and/or treatment of heart and blood vessel diseases such as thromboses, arterioscleroses, hypertension, or for inflammatory processes, allergies, cancers, viral diseases, and certain degenerative damages of the central nervous system are disclosed.

14 Claims, No Drawings

INDOLOCARBAZOLE DERIVATIVES, PROCESSES FOR THEIR PREPARATION AND COMPOSITIONS CONTAINING THEM

CROSS-REFERENCE TO RELATED APPLICATION

This application is a continuation-in-part of U.S. Ser. No. 07/484,445, filed Feb. 20, 1990, now abandoned, which is a continuation of U.S. Ser. No. 07/304,061, filed Jan. 30, 1989, now abandoned, and of U.S. Ser. No. 08/073,255, filed Jun. 7, 1993, now abandoned, which is a continuation of U.S. Ser. No. 07/424,015, filed Oct. 19, 1989, now abandoned.

TECHNICAL FIELD

This invention relates to indolocarbazole derivatives, processes for their preparation and compositions containing them.

BACKGROUND ART

Protein kinase C plays an important role in intracellular signal transduction and is closely linked to the regulation of contractile, secretory, and proliferative processes.

SUMMARY OF THE INVENTION

The present invention concerns novel indolocarbazole compounds of formula:

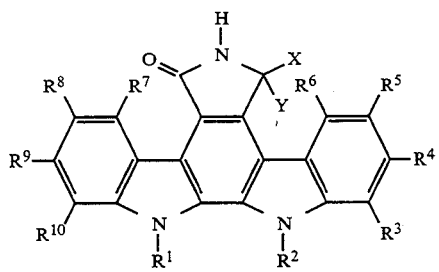

I or a pharmaceutically acceptable salt thereof. $R^1$–$R^{10}$, X, and Y are defined below.

Preferred compounds of the instant invention are those of formula I above wherein: $R^1$ and $R^2$ are each independently:
hydrogen,
methyl,
ethyl,
n-propyl,
isopropyl,
n-butyl,
cyanomethyl,
2-cyanoethyl,
benzyl,
acetyl,
methoxycarbonylmethyl,
2-methoxyethyl,
2-aminoethyl,
3-aminopropyl,
1-amino-2-propyl,
2-dimethylaminoethyl,
3-dimethylamino-1-propyl,
3-dimethylamino-2-propyl,
2-diethylaminoethyl,
2-[N-benzyl-N-methylamino]-ethyl,
3-[N-benzyl-N-methylamino]-propyl,
3-dimethylamino-2-hydroxy-1-propyl,
3-diethylamino-2-hydroxy-1-propyl,
3-diethylamino-2-methoxy-1-propyl,
2-piperidinoethyl,
3-piperidinopropyl,
2-pyrrolidinoethyl,
3-pyrrolidinopropyl,
2-morpholinoethyl,
3-morpholinopropyl,
3-morpholino-2-hydroxy-1-propyl,
pyrrolidin-2-ylmethyl, or
N-methylpyrrolidin-2-ylmethyl groups, or
$R^1$ and $R^2$ together form butylene or hydroxy-substituted propylene,
$R^3$ to $R^{10}$ are each independently:
hydrogen,
chlorine,
bromine,
methyl,
ethyl,
hydroxyl,
methoxy,
2-aminoethoxy,
3-aminopropoxy,
1-amino-2-propoxy,
2-dimethylaminoethoxy,
3-dimethylamino-1-propoxy,
3-dimethylamino-2-propoxy,
2-diethylaminoethoxy,
2-[N-benzyl-N-methylamino]-ethoxy,
3-[N-benzyl-N-methylamino]-propoxy,
3-dimethylamino-2-hydroxy-1-propoxy,
2-piperidinoethoxy,
3-piperidinopropoxy,
2-pyrrolidinoethoxy,
3-pyrrolidinopropoxy,
2-morpholinoethoxy,
3-morpholinopropoxy,
pyrrolidin-2-ylmethoxy, or
N-methylpyrrolidin-2-ylmethoxy and X and Y are both hydrogen or one of X or Y is hydrogen and the other is hydroxyl, methoxy, ethoxy, propoxy, isopropoxy, or n-butoxy.

The new indolocarbazole derivatives according to the present invention are also compounds of:

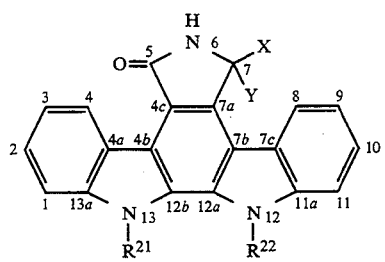

(10)

or a pharmaceutically acceptable salt thereof wherein $R^{21}$ and $R^{22}$, which can be the same or different are hydrogen atoms, straight-chained or branched alkyl radicals containing from one to six carbon atoms, benzyl radicals, unsubstituted or substituted aminoalkyl radicals containing from one to twelve carbon atoms, alkoxycarbonylalkyl radicals containing from three to six carbon atoms, —$CH_2$—CO—$NR^{23}R^{24}$ radicals, wherein $R^{23}$ and $R^{24}$ are the same or different and are hydrogen, alkyl radicals containing from one to four carbon atoms or benzyl radicals, or $R^{21}$ and $R^{22}$ are haloalkyl, hydroxyalkyl or alkoxyalkyl radicals with, in each case, of from one to six carbon atoms, benzoylalkoxyalkyl-, acetyloxyalkoxyalkyl-, or hydroxyalkoxyalkyl radical with, in each case, from one to eleven carbon atoms or acyl radicals containing from one to four carbon atoms or $R^{21}$ and $R^{22}$ together form an alkylene radical containing two to four carbon atoms which may be unsubstituted or substituted by hydroxy, alkoxy of from one to four carbon atoms or amino and X and Y are the same and both are hydrogen atoms or X and Y are different, one of them being a hydrogen atom and the other being a hydroxyl group or an alkoxy radical containing from one to four carbon atoms, with the proviso that all of $R^{21}$, $R^{22}$, X and Y are not simultaneously hydrogen.

The present invention also provides processes for the preparation of compounds of formula (10) and of regioisomeric mixtures of two of these compounds of formula (10), as well as pharmaceutical compositions containing at least one compound of formula (10). The invention also provides a method of treating diseases of blood vessels.

DESCRIPTION OF THE BEST MODE

More preferred compounds of the instant invention are those of formula I wherein $R^1$ and $R^2$ are each independently:
 methyl,
 ethyl,
 n-propyl,
 isopropyl,
 n-butyl,
 2-cyanoethyl,
 methoxycarbonylmethyl,
 benzyl,
 2-methoxyethyl,
 2-aminoethyl,
 3-aminopropyl,
 1-amino-2-propyl,
 N,N-alkylbenzyl,
 N,N-alkylbenzylaminoalkyl,
 2-dimethylaminoethyl,
 3-dimethylamino-1-propyl,
 3-dimethylamino-2-propyl,
 2-diethylaminoethyl,
 2-[N-benzyl-N-methylamino]-ethyl,
 3-[N-benzyl-N-methylamino]-propyl,
 3-diethylamino-2-hydroxy-1-propyl,
 3-diethylamino-2-methoxy-1-propyl,
 3-dimethylamino-2-methoxy-1-propyl,
 3-dimethylamino-2-hydroxy-1-propyl,
 2-piperidinoethyl,
 3-piperidinopropyl,
 2-pyrrolidinoethyl,
 3-pyrrolidinopropyl,
 2-morpholinoethyl,
 3-morpholinopropyl,
 3-morpholino-2-hydroxy-1-propyl,
 pyrrolidin-2-ylmethyl, and
 N-methyl-pyrrolidin-2-ylmethyl;
one or two of $R^3$ to $R^{10}$ are not hydrogen and are each independently methyl, ethyl, chloro, bromo, methoxy, hydroxy or unsubstituted or substituted aminoalkoxy of from 1 to 12 carbons.

Still more preferred compounds of the instant invention are those according to claim 1 wherein $R^4$ or $R^9$ is methoxy, methyl or chloro, $R^5$ and $R^8$ are both methoxy, hydroxyl, methyl, bromo or chloro, $R^4$ and $R^9$ are both methoxy, methyl, bromo, or chloro, $R^4$ and $R^5$ or $R^8$ and $R^9$ are the same and are methoxy, or $R^4$, $R^5$, $R^8$, and $R^9$ are methoxy and $R^3$, $R^6$, $R^7$, and $R^{10}$ are hydrogen.

The most preferred compounds of the instant invention are selected from the group consisting of:
 3,9-Dichloro-6,7,12,13-tetrahydro-5-oxo-5H-indolo[2,3-a]pyrrolo[3,4-c]carbazole,
 6,7,12,13-Tetrahydro-3,9-dimethoxy-5-oxo-5H-indolo[2,3-a]pyrrolo[3,4-c]carbazole,
 6,7,12,13-Tetrahydro-3,9-dimethyl-5-oxo-4H-indolo[2,3-a]pyrrolo[3,4-c]carbazole,
 3,9-Dibromo-6,7,12,13-tetrahydro-5-oxo-5H-indolo[2,3-a]pyrrolo[3,4-c]carbazole,
 2,10-Dichloro-6,7,12,13-tetrahydro-5-oxo-5H-indolo[2,3-a]pyrrolo[3,4-c]carbazole,
 1,11-Dichloro-6,7,12,13-tetrahydro-5-oxo-5H-indolo[2,3-a]pyrrolo[3,4-c]carbazole,
 6,7,12,13-Tetrahydro-9-methoxy-5-oxo-5H-indolo[2,3-a]pyrrolo[3,4-c]carbazole,
 6,7,12,13-Tetrahydro-3-methoxy-5-oxo-5H-indolo[2,3-a]pyrrolo[3,4-c]carbazole,
 2-Chloro-6,7,12,13-tetrahydro-5-oxo-5H-indolo[2,3-a]pyrrolo3,4-c]carbazole,
 10-Chloro-6,7,12,13-tetrahydro-5-oxo-5H-indolo[2,3-a]pyrrolo[3,4-c]carbazole,
 2 (and 10)-Chloro-12-ethyl-6,7,12,13-tetrahydro-5-oxo-5H-indolo[2,3-a]pyrrolo[3,4-c]carbazole,
 2 (and 10)-Chloro-12,13-diethyl-6,7,12,13-tetrahydro-5-oxo-5H-indolo[2,3-a]pyrrolo[3,4-c]carbazole,
 2 (and 10)-chloro-13-ethyl-6,7,12,13-tetrahydro-5-oxo-5H-indolo[2,3-a]pyrrolo [3,4-c]carbazole,
 12-Ethyl-6,7,12,13-tetrahydro-3,9-dimethoxy-5-oxo-5H-indolo[2,3-a]pyrrolo[3,4-c]carbazole,
 13-Ethyl-6,7,12,13-tetrahydro-3,9-dimethoxy-5-oxo-5H-indolo-[2,3-a]pyrrolo[3,4-c]carbazole,
 12-Methyl-6,7,12,13-tetrahydro-3,9-dimethyl-5-oxo-5H-indolo[2,3-a]pyrrolo[3,4-c]carbazole,
 13-Methyl-6,7,12,13-tetrahydro-3,9-dimethyl-5-oxo-5H-indolo[2,3-a]pyrrolo[3,4-c]carbazole,
 12,13-Diethyl-6,7,12,13-tetrahydro-3,9-dimethoxy-5-oxo-5H-indolo[2,3-a]pyrrolo[3,4-c]carbazole,
 12,13-Dimethyl-6,7,12,13-tetrahydro-3,9-dimethyl-5-oxo-5H-indolo[2,3-a]pyrrolo[3,4-c]carbazole,
 12,13-Dimethyl-6,7,12,13-tetrahydro-3,9-dimethoxy-5-oxo-5H-indolo[2,3-a]pyrrolo[3,4-c]carbazole, and
 6,7,12,13-Tetrahydro-3,9-dihydroxy-5-oxo-5H-indolo[2,3-a]pyrrolo[3,4-c]carbazole.

The invention also concerns a pharmaceutical composition comprising an effective amount of a compound as defined herein in combination with a pharmaceutically acceptable carrier.

The invention also concerns a method for treating and/or preventing heart and blood vessel diseases such as thrombosis, arteriosclerosis, and hypertension.

The invention also concerns a method for treating inflammatory processes, allergies, cancers, viral diseases, and certain degenerative damages of the central nervous system.

The present invention concerns new indolocarbazole derivatives of the formula I:

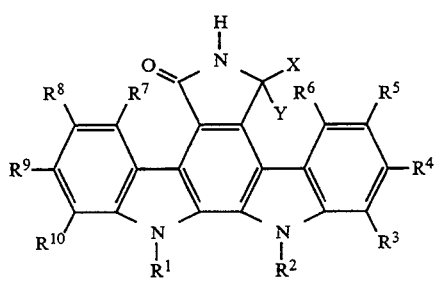

I

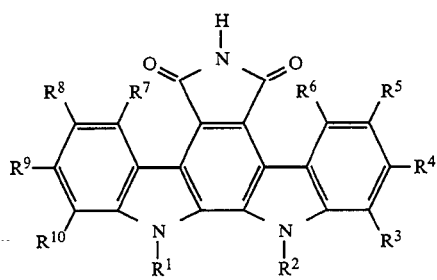

(II)

or a pharmaceutically salt thereof in which $R^1$ and $R^2$ are the same or different and are hydrogen; a straight-chained or branched alkyl with one to 18 carbon atoms; cyanoalkyl with two to four carbon atoms; benzyl unsubstituted or substituted with up to three $C_{1-4}$-alkyl groups, $C_{1-4}$-alkoxy groups or halogen atoms; aminoalkyl with up to 12 carbon atoms, unsubstituted on the nitrogen atom or mono- or disubstituted by benzyl or alkyl with one to four carbon atoms or in the case of the two substituents or one substituent on the nitrogen atom form with a substituent of the alkyl chain and together with the nitrogen atom a heterocyclic ring with three to six carbon atoms which can also contain oxygen, sulfur, and/or further nitrogen atoms and can be substituted by alkyl groups with one to four carbon atoms, whereby the alkyl chain can be substituted by further $C_{1-4}$-alkyl, hydroxyl, or a $C_{1-4}$-alkoxy, alkoxycarbonylalkyl with up to seven carbon atoms, $-CH_2-CO-NR_{11}R_{12}$, in which $R_{11}$ and $R_{12}$ are the same or different and are hydrogen, alkyl with one to six carbon atoms or benzyl, haloalkyl, hydroxyalkyl or alkoxyalkyl with, in each case, up to six carbon atoms, acyl group with one to four carbon atoms or $R^1$ and $R^2$ together form an alkylene group with two to four carbon atoms which can possibly be substituted by hydroxyl, alkoxy with one to four carbon atoms or amino unsubstituted or mono- or disubstituted by benzyl or alkyl with one to four carbon atoms, X and Y are either the same and are hydrogen or X and Y are different, and one is hydrogen and the other hydroxy or alkoxy of from one to four carbon atoms; $R^3$, $R^4$, $R^5$, $R^6$, $R^7$, $R^8$, $R^9$, and $R^{10}$ are each independently hydrogen, $C_{1-4}$-alkyl, $C_{1-4}$-alkoxy, $C_{1-4}$-acyl, halogen (especially chlorine or bromine), nitro, amino unsubstituted or mono- or disubstituted by benzyl or alkyl of from one to four carbon atoms, benzyloxy, hydroxyl, aminoalkoxy of from one to 12 carbon atoms, unsubstituted on the nitrogen atom or mono- or disubstituted by benzyl or alkyl with one to four carbon atoms or in the case of the two substituents or one substituent on the nitrogen atom form with a substituent of the alkyl chain and together with the nitrogen atom a heterocyclic ring with three to six carbon atoms which can also contain oxygen, sulfur, and/or further nitrogen atoms and can be substituted by alkyl of from one to four carbon atoms, whereby the alkyl chain can be substituted by further $C_{1-4}$-alkyls, hydroxy, or a $C_{1-4}$-alkoxy group, trifluoromethyl, or two neighboring radicals together signify a methylenedioxy group, with the proviso that at least one and up to four of $R^3$ to $R^{10}$ are different from hydrogen.

The invention also concerns a process for the preparation of the compounds of formula I or of regioisomeric mixtures of these compounds I, characterized in that one either a) reduces imides of the formula II:

in which $R^1$ to $R^{10}$ have the above-mentioned meaning, with zinc or zinc amalgam in the presence of an organic or inorganic acid to compounds of formula I, wherein X and Y are hydrogen, or b) reduces imides of formula II, in which $R^1$ to $R^{10}$ have the above-mentioned meaning, with zinc or zinc amalgam in the presence of an inorganic acid, with borohydrides or with lithium aluminum hydride to compounds of formula I, in which X or Y is hydroxyl and the other is hydrogen, or, when the reduction is carried out in $C_{1-4}$-alcohols, also to compounds of formula I, in which X or Y signifies a $C_{1-4}$-alkoxy group and the other residue hydrogen, or modifies compounds of formula I, in which X or Y is hydroxyl and the other hydrogen, by acid-catalyzed reaction with $C_{1-4}$-alcohols to compounds of formula I, in which X or Y is $C_{1-4}$-alkoxy group and the other is hydrogen, or c) alkylates or acylates in a known manner, on one or both indole nitrogen atoms, compounds of formula I, in which X, Y, $R^1$, and $R^2$ are hydrogen, with one or two equivalents of a compound of formula III:

$$R^{13}-X^2 \qquad (III)$$

in which $R^{13}$ is a straight-chained or branched alkyl group with one to 18 carbon atoms, an unsubstituted or substituted benzyl, an aminoalkyl group from one to 12 carbon atoms unsubstituted or substituted on the nitrogen atom, whereby the alkyl chain can be substituted by further $C_{1-4}$-alkyl, hydroxy, or $C_{1-4}$-alkoxy, alkoxycarbonylalkyl from one to six carbon atoms, haloalkyl or alkoxyalkyl with, in each case, from one to six carbon atoms, acyl with one to four carbon atoms, and $X^2$, preferably for halogen, especially iodine, bromine or chlorine, in the presence of one or two equivalents of a base, or in that one modifies an already introduced $R^{13}$ by usual methods of organic chemistry (e.g., Houben-Weyl, *Methoden der Organischen Chemie*, Georg Thieme Verlag, Stuttgart, 1966) to one of the residues $R^1$ and $R^2$, e.g., by hydrolysis, ether splitting, amide formation or reduction, or d) alkylates or acylates compounds of formula I, in which X, Y, and one of the residues $R^1$ and $R^2$ is hydrogen, with an equivalent of a compound of formula III in the presence of a base analogously to process C and optionally modifies an introduced $R^{13}$, as described in process C, to one of $R^1$ or $R^2$, or e) compounds of formula I, which X and Y is hydrogen and $R^1$ and/or $R^2$ is a N,N-disubstituted 3-amino- 2-hydroxy-1-propyl group, by alkylation of compounds of formula I, in which $R^1$ and/or $R^2$, as well as X and Y is hydrogen, with 1,1-disubstituted 3-hydroxyazetidinum halides (*J Org Chem* 523, 1968), or f) compounds of formula I, in which X and Y are hydrogen and $R^1$ or $R^2$ 2-cyanoethyl or 2-alkoxycarbonylethyl with from one to seven carbon atoms, by base catalyzed Michael-addition of compounds of formula I, in which $R^1$ and/or $R^2$, as well as X and Y is hydrogen, on activated olefins of formula VIII:

$$CH_2=HC-R^{14} \qquad (VIII)$$

in which $R^{14}$ is a cyano group or an alkoxycarbonyl group with from one to five carbon atoms, or g) compounds of formula I, in which X and Y are hydrogen and $R^1$ or $R^2$ together form a propylene group of formula IX:

$$-CH_2-\underset{R}{CH}-CH_2- \qquad (IX)$$

in which R is hydroxy, $C_{1-4}$-alkoxy or amino, by reaction of compounds of formula I, in which $R^1$ and $R^2$, as well as X and Y is hydrogen, with two equivalents of a base and epichlorohydrin or epibromohydrin, whereby the hydroxy substituted propylene residue formed first may be reacted by known methods to $C_{1-4}$-alkoxy- or amino-substituted propylene residues.

Compounds of the formula I, in which $R^1$ and/or $R^2$ is a methyl or ethyl group, may be prepared in known manner by alkylation with dimethyl- or diethylsulfate.

The disclosed methods of the alkylation or acylation of compounds of the general formula I, in which $R^1$ and $R^2$, as well as X and Y signifies hydrogen, are surprising, because it was unforeseeable that the introduction of one or two alkyl or acyl residues selectively takes place on the indolonitrogen atom and not on the nitrogen atom of the lactame ring.

The preparation of the compounds of the general formula II, in which $R^1$ and $R^2$ represent hydrogen, takes place in analogy to the processes described in the literature (*Tetrahydron Lett* 1441, 1983, *Tetrahydron* 44:2887, 1988, and *Angew Chem* 92:463, 1980; *J Org Chem* 1177, 1987; *Tetrahedron Lett* 441, 1987, and B. Pelcman, Dissertation Stockholm; European Patent application 0269025 and *Tetrahedron Lett* 4015, 1985).

Compounds of the general formula II, in which $R^1$ and $R^2$ are the same or different and signify hydrogen, a straight-chained or branched alkyl group with one to 18 carbon atoms, a benzyl group unsubstituted or substituted with up to three $C_{1-4}$-alkyl groups, $C_{1-4}$-alkoxy groups or halogen atoms, or an alkoxyalkyl radical with up to six carbon atoms and $R^3$ to $R^{10}$, independently of one another, signify hydrogen, $C_{1-4}$-alkyl, $C_{1-4}$-alkoxy, halogen, especially chlorine or bromine, a benzyloxy group, a hydroxyl group, a trifluoromethyl group or two neighboring residues together signify a methylenedioxy group, with the proviso that at least one and up to four of the residues $R^3$ to $R^{10}$ are different from hydrogen, can, in modification of the syntheses of arcyriarubins or of arcyriaflavines (cf. Steglich et al, *Angew Chem* 92:463, 1980 and *Tetrahedron* 44:2887, 1988), be prepared as follows (cf. Synthesis Scheme 1).

Synthesis Scheme 1

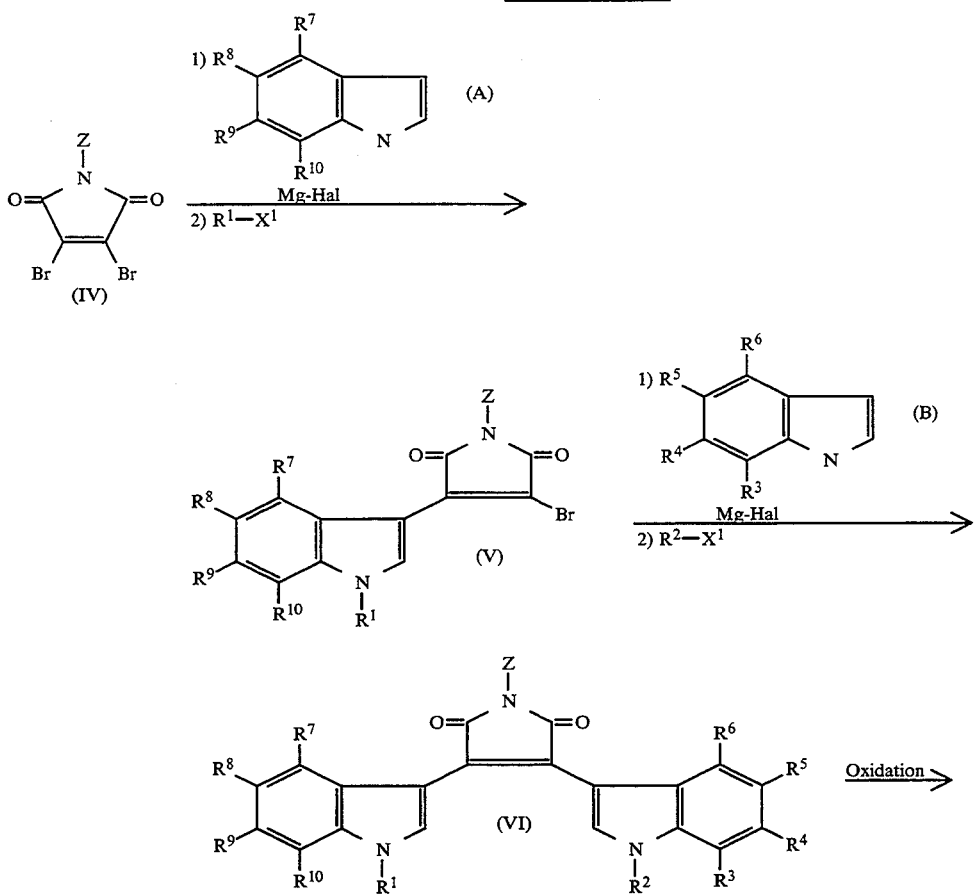

-continued
Synthesis Scheme 1

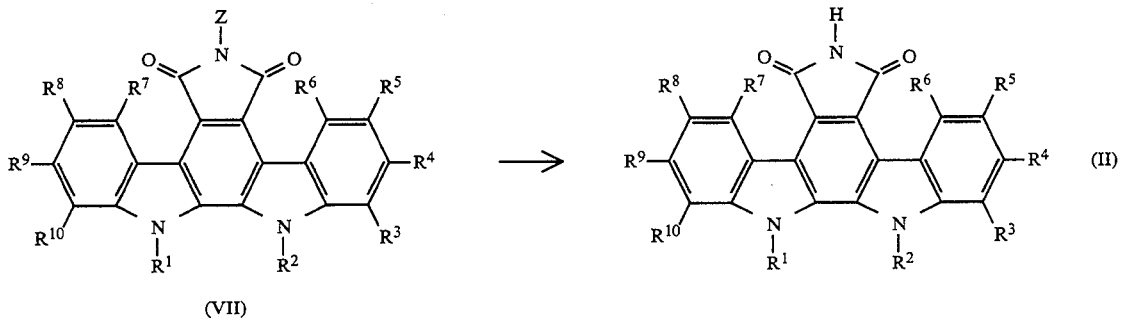

(VII)

A dibromomaleinimide (IV) suitably substituted on the nitrogen is reacted with a substituted indole Grignard reagent A. The product obtained, formula V, in which $R^1$ is hydrogen, is possibly alkylated on the indole nitrogen with an alkylation agent $R^1$-$X^1$, whereby, with the exception of hydrogen, $R^1$ has one of the mentioned meanings and $X^1$ stands for an easily removable group, such as chlorine or bromine, whereby a product of formula V is obtained, in which $R^1$ is different from hydrogen. Renewed reaction of product V with a substituted indole Grignard reagent B and possibly subsequent alkylation with an alkylation agent of formula $R^2$—$X^1$, in which $R^2$, with the exception of hydrogen, has one of the mentioned meanings and $X^1$ stands for an easily removable group, such as chlorine or bromine, leads to a product of formula VI. This is cyclized according to literature instructions, thereafter the substituted imide group in compound VII is converted by suitable processes into the unsubstituted imide group of the compound II. If Z signifies methyl, then the corresponding N-methylimide can be converted according to literature instructions (*Tetrahedron* 44:2887, 1988) into the unsubstituted imide.

Compounds of formula I are preferred in which $R^1$ and/or $R^2$ signify straight-chained or branched alkyl groups with one to four carbon atoms, especially methyl, ethyl, n-propyl, isopropyl, and n-butyl, 2-cyanoethyl groups, methoxcarbonylmethyl groups, benzyl groups, 2-methoxyethyl groups, acetyl groups or also an alkylene group with two to four carbon atoms which $R^1$ and $R^2$ form together, especially the butylene group or a hydroxy-substituted propylene group, or unsubstituted or substituted aminoalkyl groups with up to 12 carbon atoms, such as unsubstituted aminoalkyl groups, especially 2-aminoethyl, 3-aminopropyl, 1-amino-2-propyl, N,N-dialkylaminoalkyl or N,N-alkylbenzyl or N,N-alkylbenzylaminoalkyl groups with $C_1$-$C_4$-alkyl substituents on the nitrogen atom and one to four carbon atoms in the alkyl chain, whereby the alkyl chain can be substituted by further $C_{1-4}$-alkyl radicals, a hydroxyl group or a $C_{1-4}$-alkoxy group, especially 2-dimethylaminoethyl, 3-dimethylamino-1-propyl, 3-dimethylamino-2-propyl, 2-diethylaminoethyl, 2-[N-benzyl-N-methylamino]-ethyl, 3-[N-benzyl-N-methylamino]-propyl, 3-diethylamino2-hydroxy-1-propyl, 3-diethylamino-2-methoxy-1-propyl, 3-dimethylamino-2-methoxy-1-propyl, 3-dimethylamino2-hydroxy-1-propyl or 2-piperidinoethyl, 3-piperidinopropyl, 2-pyrrolidinoethyl, 3-pyrrolidinopropyl, 2-morpholinoethyl, 3-morpholinopropyl, 3-morpholino2-hydroxy-1-propyl, pyrrolidin-2-ylmethyl and N-methylpyrrolidin-2-ylmethyl groups and one or two of the residues $R^3$ to $R^{10}$ are different from hydrogen and independently of one another, are methyl, ethyl, chloro, bromo, methoxy, hydroxy or unsubstituted or substituted aminoalkoxy groups with up to 12 carbon atoms, whereby the aminoalkyl radicals correspond to those which are defined as especially suitable for $R^1$ and/or $R^2$.

Compounds of formula I are especially preferred in which $R^5$ or $R^8$ stand for methoxy, methyl or chloro or in which $R^4$ or $R^9$ stand for methoxy, methyl or chloro or in which $R^5$ and $R^8$ are the same and stand for methoxy, hydroxyl, methyl, bromo or chloro or in which $R^4$ and $R^9$ are the same and stand for methoxy, methyl, bromo or chloro or in which $R^3$ and $R^{10}$ are the same and stand for methyl, bromo or chloro or in which $R^4$ and $R^5$ or $R^8$ and $R^{10}$ are the same and stand for methoxy or in which $R^4$, $R^5$, $R^8$, and $R^9$ are the same and stand for methoxy and the other residues $R^3$ to $R^{10}$ are each hydrogen.

Zinc amalgam/hydrogen chloride gas in C1-C4 alcohols, zinc amalgam in glacial acetic acid or zinc in glacial acetic acid are preferred for the reduction of process A. In order to reduce to the stage of the lactam, it is preferred to work at an elevated temperature of about 50° C. to 150° C. This reduction has hitherto been described on indolocarbazoles only for one derivative which is protected on the imide nitrogen atom by a benzyl group (*J Org Chem* 1177, 1987 and *Tetrahedron Lett* 1441, 1983).

For the carrying out of the reductions according to process B, there is preferably used zinc amalgam/hydrogen chloride gas in C1-C4 alcohols at temperatures below 20° C. or borohydrides, such as e.g., sodium borohydride, preferably in C1-C4 alcohols or alcohol/water mixtures, or lithium aluminum hydride in an aprotic solvent. Compounds of the general formula I, in which X or Y signifies $C_{1-4}$-alkoxy group and the other residue signifies hydrogen, are e.g., obtained the reduction is carried out with zinc amalgam/hydrogen chloride gas in C1-C4 alcohols at 0° C.

If, in the case of the reduction with zinc amalgam/hydrogen chloride gas in C1-C4 alcohols, mixtures of compounds of the general formula I are obtained, in which X or Y signifies either a hydroxyl or a C1-C4 alkoxy group and the other of the two residues signifies hydrogen, these can be separated by usual processes, such as crystallization or chromatography.

Compounds of formula I, in which X or Y is hydroxyl or C1-C4 alkoxy group and $R^1$ and/or $R^2$ is hydrogen, can subsequently possibly by alkylated or acylated by processes C to D to compounds of formula I, in which X or Y are hydroxyl or C1-C4 alkoxy group and the other of the two residues hydrogen and $R^1$ and $R^2$ one of the above-given definitions but both not simultaneously hydrogen.

For the carrying out of the alkylations or acylations according to process C or D with compounds III, or by process E and G, especially suitable bases or hydrides, carbonates, hydroxides, oxides or alkoxides of the alkali or alkaline earth metals or organo-lithium compounds.

A base especially suitable for the Michael-addition is 1,8-diazabicyclo[5,4,o]undec-7-en (DBU).

Compounds of formula I according to processes A to F which are obtained as regioisomeric mixtures can be used in the form of the regioisomeric mixtures. The regioisomers can be separated by known separation processes, such as crystallization or chromatography.

Compounds of formula I, in which one or up to four of the residue $R^3$ to $R^{10}$ is a hydroxyl group, can also be prepared in a known manner by either splitting of compounds of formula I, in which one or more of the residues $R^3$ to $R^{10}$ stand for a C1-C4 alkoxy group.

Compounds of formula I, in which one or up to four of the residues $R^3$ to $R^{10}$ are an unsubstituted or substituted aminoalkoxy group, can also be prepared in a known manner by aminoalkylation of compounds of formula I, in which one or up to four of the residues $R^3$ to $R^{10}$ is hydroxyl.

Compounds of formula I, in which X and Y are hydrogen and one or two of the residues $R^3$ to $R^{10}$ is $C_{1-4}$-alkyl, $C_{1-4}$-acyl, chloro, bromo or nitro, can also be prepared according to known methods of electrophilic aromatic substitution from compounds of formula I, in which X and Y are hydrogen and one or both corresponding residues $R^3$ to $R^{10}$ are hydrogen.

Compounds of formula I which have a chiral center can be used as stereoisomeric mixtures or in the form of the enantiomers. The enantiomers can be obtained according to the processes usual for optical separations of stereoisomers.

Radicals which are especially preferred for $R^{21}$ and/or $R^{22}$ include straight-chained and branched alkyl radicals containing from one to four carbon atoms, especially methyl, ethyl, n-propyl, isopropyl and n-butyl radicals, methoxycarbonylmethyl radicals, benzyl radicals, 2-methoxyethyl radicals, acetyl radicals and also alkylene radicals containing two to four carbon atoms and especially a butylene radical or hydroxysubstituted propylene radical which $R^{21}$ and $R^{22}$ form together.

The preparation of the compounds of formula (10) takes place, depending upon the substitution, according to one of the processes described hereinafter:

(h) when X and Y are hydrogen atoms and $R^{21}$ and $R^{22}$ are the same but are not hydrogen atoms or one of $R^{21}$ and $R^{22}$ is hydrogen, a compound of formula (10) can be obtained by alkylating or acylating the indolocarbazole of formula 11:

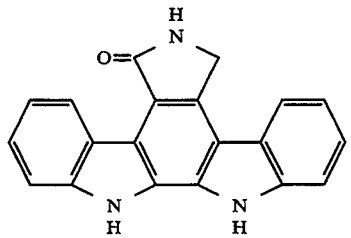

(11)

on one or both indole nitrogen atoms with one or two equivalents of a compound of the general formula 12:

$$R^{25}-X \qquad (12)$$

in which $R^{25}$ is a straight-chained or branched alkyl radical containing from one to six carbon atoms, an unsubstituted or substituted aminoalkyl radical containing from one to twelve carbon atoms, an alkoxycarbonylalkyl radical containing from one to six carbon atoms, a haloalkyl or alkoxyalkyl radical containing, in each case, from one to six carbon atoms, a benzoylalkoxyalkyl or acetyloxyalkoxyalkyl radical with, in each case, from one to eleven carbon atoms or an acyl radical containing from one to four carbon atoms and X preferably is a halogen atom, especially an iodine, bromine or chlorine in the presence of one or two equivalents of a base, for example, an alkali metal or alkaline earth metal hydride, carbonate, hydroxide, oxide or alkoxide, or of an organolithium compound, in known manner; or by modifying an already introduced radical $R^{25}$ by conventional methods of preparative organic chemistry (see Houben-Weyl, Methoden der Organischem Chemie, pub. Georg Thieme Verlag, Stuttgart, 1966) to one of the radicals $R^{21}$ or $R^{22}$, for example by hydrolysis, ether cleavage, amide formation or reduction.

Thus, compounds of formula (I), in which $R^1$ and/or $R^2$ is a $-CH_2-CO-NR^3R^4$ radical, are preferably prepared by reacting compounds of formula (I), in which $R^1$ and/or $R^2$ is an alkoxycarbonylmethyl radical, with an amine of formula $HNR^3R^4$, wherein $R^3$ and $R^4$ have the above meanings.

Compounds of formula (10), wherein $R^{21}$ and/or $R^{22}$ are hydroxyalkyl radicals, are preferably prepared by hydrolyzing compounds of formula (10), wherein $R^{21}$ and/or $R^{22}$ is a haloalkyl radical and especially bromoalkyl or chloroalkyl radical, or by ether cleavage of compounds of formula (10), wherein $R^{21}$ and/or $R^{22}$ is an alkoxyalkyl radical.

Compounds of formula (10), wherein $R^{21}$ and/or $R^{22}$ are hydroxyalkoxyalkyl radicals, are preferably prepared by methods known per se from compounds of formula (10), wherein $R^{21}$ and/or $R^{22}$ is a benzoyloxyalkoxyalkyl or acetyloxyalkoxyalkyl radical. Preferred hydroxyalkoxyalkyl radicals are 2-hydroxyethoxymethyl and 3-hydroxypropoxymethyl radicals.

Compounds of formula (10), wherein $R^{21}$ and/or $R^{22}$ are N,N-disubstituted 3-amino-2-hydroxypropyl radicals, are preferably prepared by alkylation of indolocarbazole compounds of formula (11) with 1,1-disubstituted 3-hydroxyazetidinium halogenides (J. Org. Chem. 1968, 523).

Compounds of formula (10), in which $R^{21}$ and $R^{22}$ together form an alkylene radical $-(CH_2)_n-$, wherein n is 2, 3 or 4, are obtained by reacting the indolocarbazole of formula (11) with two equivalents of one of the above-mentioned bases and one equivalent of a dihaloalkane and preferably of a dibromoalkane.

Compounds of formula (10), wherein $R^{21}$ and $R^{22}$ together form a propylene radical of formula V:

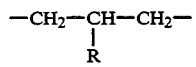

wherein R is hydroxy, $C_{1-4}$-alkoxy or amino, are prepared by reaction of the indolocarbazole of formula (11) with two equivalents of one of the above mentioned bases and epichlorohydrin or epibromohydrin, whereby the primarily obtained hydroxy substituted propylene radical is reacted by methods known per se into $C_{1-4}$-alkoxy or amino substituted propylene radicals.

Compounds of formula (10), wherein $R^{21}$ and/or $R^{22}$ are methyl or ethyl radicals, can also be prepared by alkylating with dimethyl or diethyl sulfate in known manner.

The above-described process of alkylating or acylating the indolocarbazole of formula (11) in the presence of a base with an alkylating or acylating agent is surprising because it was not to have been foreseen that the introduction of one or two radicals $R^{25}$ would take place selectively on the indole nitrogen atom but not on the nitrogen atom of the lactam ring.

(i) When X and Y both are hydrogen atoms and $R^{21}$ and $R^{22}$ are different and neither of them is a hydrogen atom, compounds of formula (10) can be prepared by reacting a compound of formula (10), which has been prepared according to process h) in which either $R^{21}$ or $R^{22}$ has one of the meanings given for $R^{25}$ and the other is a hydrogen atom, with a compound of formula (12), in which $R^{25}$ has another meaning given for $R^{25}$, in the presence of a base in a manner analogous to that described for process h) and, if desired, one or both of the radicals with the meaning of $R^{25}$ is modified, as described in process h), to give one of the radicals $R^{21}$ or $R^{22}$.

(j) Compounds of formula (10), wherein X or Y is a hydroxyl group and the other one of two symbols is a hydrogen atom, can be prepared by reduction of the imide of the formula 13:

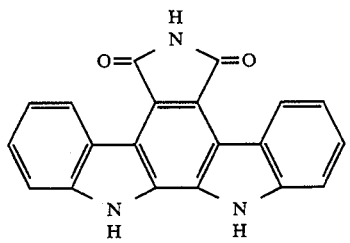

(13)

Preferred reducing agents include zinc amalgam/gaseous hydrogen chloride in a $C_1$-$C_4$-alcohol and zinc amalgam n glacial acetic acid.

Compounds of formula (10), wherein X or Y is a $C_{1-4}$-alkoxy radical and the other one is a hydrogen atom, can be prepared either by reduction of the imide of formula (13) in a $C_1$-$C_4$-alcohol, preferably with zinc amalgam/gaseous hydrogen chloride, or by acid-catalyzed reaction of a compound of formula (10), wherein X or Y is a hydroxyl group and the other one is a hydrogen atom, with a $C_1$-$C_4$-alcohol in an anhydrous medium.

If, in the case of the reduction with zinc amalgam/gaseous hydrogen chloride in a $C_1$-$C_4$-alcohol, a mixture of compounds of formula (10) is obtained, X or Y is either a hydroxyl group or a $C_1$-$C_4$-alkoxy radical and the other one is a hydrogen atom, these can be separated by conventional processes, for example, crystallization or chromatography.

A compound of formula (10) so produced, wherein X or Y is a hydroxyl group or a $C_1$-$C_4$-alkoxy radical and $R^{21}$ and $R^{22}$ are hydrogen atoms, can, if desired, be alkylated or acylated according to process h) or i) to give a compound of formula (10), wherein X or Y is a hydroxyl group or a $C_1$-$C_4$-alkoxy radical and the other one is a hydrogen atom and $R^1$ and $R^2$ have the meanings given above except that they are not both hydrogen atoms.

Unsubstituted and substituted aminoalkyl radicals containing up to 12 carbon atoms which are especially preferred for $R^{21}$ and/or $R^{22}$ include unsubstituted aminoalkyl radicals, such as 2-aminoethyl, 3-aminopropyl, and 1-amino-2-propyl radicals, N,N-dialkylamino and N,N-aklylbenzylaminoalkyl radicals with $C_1$-$C_4$-alkyl substituents on the nitrogen atoms and up to four carbon atoms in alkyl chain, in which the alkyl chains can be substituted by further $C_1$-$C_4$-alkyl radicals or by a hydroxyl group, especially a dimethylaminoethyl, 3-dimethylamino-1-propyl, 3-dimethylamino-2-propyl, 2-diethylaminoethyl, 2-[N-benzyl-N-methylamino]-ethyl, 3-[N-benzyl-N-methylamino]-propyl or 3-dimethylamino-2-hydroxy-1-propyl radical, a 3-diethylamino-2-hydroxy-1-propyl, 3-piperidino-2-hydroxy-1-propyl, 3-dimethylamino-2-methoxy-1-propyl, 3-diethylamino-2-methoxy-1-propyl, 3-piperidino-2-methoxy-1-propyl, 3-(N-benzyl-N-methylamino)-2-methoxy-1-propyl, 3-(N-benzyl-N-methylamino)-2-hydroxy-1-propyl, 3-(N-methylamino)-2-methoxy-1-propyl, 3-(N-methylamino)-2-hydroxy-1-propyl, 4-dimethylamino-3-methoxy-2-butyl radical or a 2-piperidinoethyl, 3-piperidinopropyl, 2-pyrrolidinoethyl, 3-pyrrolidinopropyl, 2-morpholinoethyl, 3-morpholinopropyl, pyrrolidin-3-ylmethyl or N-methyl-pyrrolidin-2-ylmethyl, piperidin-2-ylmethyl, N-methyl-piperidin-2-ylmethyl radical or a piperazinoalkyl radical with one to four carbon atoms in the alkyl chain, unsubstituted or substituted at the nitrogen atom by $C_{1-4}$-alkyl.

Further radicals which are especially preferred for $R^{21}$ and/or $R^{22}$ include straight-chained and branched alkyl radicals containing up to four carbon atoms, especially methyl, ethyl, n-propyl, isopropyl and n-butyl radicals, methoxycarbonylmethyl radicals, benzyl radicals, 2-methoxyethyl radicals, acetyl radicals and also alkylene radicals containing two to four carbon atoms and especially a butylene or hydroxysubstituted propylene radical which $R^{21}$ and $R^{22}$ form together.

Compounds of formula (10) obtained according to processes h), i) and j), in which $R^{21}$ and $R^{22}$ are different, can be used as regioisomeric mixtures. By means of known separation processes, such as crystallization or chromatography, the two regioisomers can be separated.

Compounds of formula (10) obtained according to process j) which have a chiral center on C7 can be used as stereoisomeric mixtures or in the form of the enantiomers. The enantiomers can be obtained according to the processes normally employed for the optical separation of stereoisomers.

Basic compounds of formula I or 10 which have a basic center on at least one of the residues $R^1$ to $R^{10}$ and $R^{21}$ and $R^{22}$, respectively, are for the purpose of purification and for galenical reasons, preferably converted into crystalline, pharmacologically acceptable salts. The salts are obtained in the usual way by neutralization of the bases with corresponding inorganic or organic acids. Acids are, for example, hydrochloric acid, sulfuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid. The acid-addition salts are, as a rule, obtained in a known manner by mixing of the free base or its solution with the corresponding acid or its solutions in an organic solvent, for example, a lower alcohol such as methanol, ethanol or 2-propanol, or a lower ketone such as acetone or 2-butanone, or an ether such as diethyl ether, diisopropyl ether, tetrahydrofuran, or dioxan.

The preparation of the indolocarbazoles used as starting materials of formulae (11) and (13) is described in the literature or can be carried out in an analogous way (Heterocylces, 20, 469/1983; and Tetrahydron Letters, 1983, 1441).

The compounds according to the invention are potent inhibitors of protein kinases, such as protein kinase C. Thus, e.g., the compound of Example 3.a shows, in the enzyme assay of protein kinase C activated with phosphatidylserine and diacylglycerol, a 50% inhibition at a concentration of 0.31 μmole/liter. The experiment was carried out according to EP-OS 0,255,126 (inhibition of protein kinase C). Admittedly, indolocarbazoles have already been described as inhibitors of protein kinase C (*J Antibiotic* 30:275, 1977; *Biochem Biophys Res Commun* 135:397, 1986). However, it is thereby mainly a question of indolocarbazole-N,N-glycosides of microbial or semisynthetic origin.

Protein kinase C plays an important role in intracellular signal transduction and is closely linked with the regulation of contractile, secretory, and proliferative processes. The compounds of the instant invention can be used for the treatment of heart and blood vessel diseases such as thromboses, arterioscleroses, hypertension, of inflammatory processes, allergies, cancers, viral diseases, and certain degenerative damages of the central nervous system. The compounds can be administered in the particularly suitable formulation enterally or parenterally in doses of 1 to 500 mg/kg, preferably of 1 to 50 mg/kg.

The compounds of formulas I or 10, according to the invention, can be administered orally or parenterally in liquid or solid form. As injection solution, there is particularly used water which contains the additives usual in the case of injection solutions, such as stabilizing agents, solubilizing agents, or buffers.

Such additives are e.g., tartrate and citrate buffers, ethanol, complex formers (such as ethylenediamine-tetraacetic acid and its nontoxic salts), as well as high molecular polymers (such as liquid polyethylene oxide) for viscosity regulation. Solid carrier materials are e.g., starch, lactose, mannitol, methyl cellulose, talc, highly dispersed silicic acids, high molecular fatty acids (such as stearic acid), gelatine, agar-agar, calcium phosphate, magnesium stearate, animal and vegetable fats, solid high molecular polymers (such as polyethylene glycol); compositions suitable for oral administration can, if desired, contain additional flavoring and/or sweetening materials.

The following examples serve for the more detailed explanation of the invention:

EXAMPLE 1

(According to process A)

3,9-Dichloro-6,7,12,13-tetrahydro-5-oxo-5H-indolo [2,3-a]pyrrolo[3,4-c]carbazole.

2.5 g (38 mmole) zinc powder and 0.25 g (0.9 mmole) mercury (II) chloride are stirred in 3 ml water for 20 minutes at 20° C., then two crops of concentrated hydrochloric acid added thereto and further stirred for one minute. Immediately thereafter, the zinc powder is washed first with water, then with ethanol, and finally with dried ethanol. The zinc powder is suspended in 50 ml dry ethanol. While stirring, 0.465 g (1.18 mmole) 3,9-dichloro-6,7,12,13-tetrahydro-5,7-dioxo-5H-indol-[2,3-a]pyrrolo[3,4-c]carbazole are added thereto and it is heated under reflux for two hours with slow passing through of dry hydrogen chloride. After cooling, it is evaporated and the residue partitioned between potassium carbonate solution (150 ml) and ethyl acetate (300 ml). The organic phase is separated off, dried over sodium sulfate, and evaporated. The residue is stirred hot with diisopropyl ether/ethyl acetate and, after cooling, the crystals filtered off. One obtains 3,9-dichloro-6,7,12,13-tetrahydro-5-oxo-5H-indolo[2,3-a]pyrrolo[3,4-c] carbazole in the form of pale beige crystals which decompose at >300° C.

The 3,9-dichloro-6,7,12,13-tetrahydro-5,7-dioxo-5H-indolo[2,3-a]pyrrolo[3,4-c]carbazole used as starting product is prepared as follows:

1.19 g (3 mmole) 3,9-dichloro-4c,6,7,7a,12,13-hexahydro-5,7-dioxo-5H-indolo[2,3-a]pyrrolo[3,4-c]carbazole and 0.70 g (3.1 mmole) DDQ are boiled under reflux for 16 hours in 100 ml ethyl acetate. After cooling, the crystals are filtered off. One obtains 3,9-dichloro-6,7,12,13-tetrahydro-5,7-dioxo-5H-indolo [2,3a]pyrrolo[3,4-c]carbazole in the form of yellow crystals which decomposes at >300° C.

The 3,9- dichloro-4c,6,7,7a,12,13-hexahydro-5,7-dioxo-5H-indolo [2,3-a]pyrrolo[3,4-c]carbazole used as starting product is prepared as follows:

8.1 g (18.8 mmole) 5-[(4-chlorophenyl)-azo]-6-[N'-(4-chlorophenyl)-hydrazino]-1,3,3a,4,7,7a-hexahydro-1,3-dioxoisoindole are boiled under reflux for 24 hours under argon atmosphere in 100 ml nitromethane with polyphosphoric acid trimethylsilyl ester (PPSE) which is freshly prepared according to literature instructions (*Bull Chem Soc JPn* 59:2171, 1986) from 18 g (127 mmole) phosphorus pentoxide and 50 ml (235 mmole) hexamethyldisiloxane in 100 ml dichloromethane. After cooling, 100 ml water are added dropwise thereto with stirring and the precipitated crude product filtered off. Subsequently, it is chromatographed on silica gel with toluene/ethyl acetate 1:1, the fraction with the R$_f$ of 0.5 isolated, stirred up with dichloromethane/methanol, and the crystals filtered off. One obtains 3,9-dichloro-4c,6,7,7a,12,13-hexahydro-5,7-dioxo-5H-indolo[ 2,3-a]pyrrolo[3,4-c]carbazole in the form of yellow crystals of the melting point >300° C.

The 5-[(4-chlorophenyl)-azo]-6-[N'-(4-chlorophenyl)-hydrazino]-1,3,3a,4,7,7a-*hexahydro*-1,3dioxoisoindole used as starting product is prepared as follows:

8 g (24.4 mmole) 1,3,3a,4,7,7a-hexahydro-1,3-dioxo-5,6-bis(trimethylsiloxy)-isoindole and 11.4 g (80 mmole) 4-chlorophenyl hydrazine are boiled under reflux for 16 hours in 50 ml methanol and 50 ml glacial acetic acid. The crystals precipitated out after cooling are filtered off, after-washed several times with methanol, and dried. One obtains 5-[(4-chlorophenyl)-azo]-6-[N'-(4-chlorophenyl)-hydrazino]-1,3,3a,4,7,7a-hexahydro-1,3-dioxoisoindole in the form of yellow-green crystals.

The 1,3,3a,4,7,7a-*hexahydro*-1,3-dioxo-5,6-bis-(trimethylsiloxy)-isoindole used as starting product is prepared as follows according to B. Pelcman (Dissertation Stockholm 1988, The Royal Institute of Technology, Department of Organic Chemistry): 75.2 g (0.326 mole), 2,3-bis-(trimethylsiloxy)-1,3-butadiene (*Chem Lett* 1219, 1977) and 31.6 g (0.326 mole) maleic acid imide are boiled under reflux for 16 hours in 1l toluene. After cooling, it is filtered, the filtrate evaporated in a vacuum, and the residue crystallized from 600 ml cyclohexane. One obtains 1,3,3a,4,7,7a-*hexahydro*-1,3-dioxo-5,6-bis(trimethylsiloxy)-isoindole in the form of colorless crystals.

The following compounds are obtained in an analogous manner:

6,7,12,13-Tetrahydro-3,9-dimethoxy-5-oxo-5H-indolo-[2,3-a]pyrrolo[3,4-c]carbazole (1.a), mp >300° C. from ethyl acetate, 6,7,12,13-Tetrahydro-3,9-dimethyl-5-oxo-4H-indolo-[2,3-a]pyrrolo[3,4-c]carbazole (1.b), mp >300° C. (decomp.) from diisopropyl ether/ethyl acetate, 3,9-Dibromo-6,7,12,13-tetrahydro-5-oxo-5H-indolo-[2,3-a]pyrrolo[3,4-c]carbazole (l.c), mp >300° C. (decomp.) from diisopropyl ether/ethyl acetate, 2,10-dichloro-6,7,12,13-tetrahydro-5-oxo-5H-indolo-[2,3-a]pyrrolo[3,4-c]carbazole (l.d), and 1,11-dichloro-6,7,12,13-tetrahydro-5-oxo-5H-indolo-[2,3-a]pyrrolo[3,4-c]carbazole (1.3), mp >340° C. from ethanol.

Example 2

(according to process A)

6,7,12,13-Tetrahydro-9-methoxy-5-oxo-5-H-indolo[2,3-a]pyrrolo[3,4-c]carbazole and
6,7,12,13-Tetrahydro-3-methoxy-5-oxo-5H-indolo[2,3-a]pyrrolo[3,4-c]carbazole.

265 mg (0.75 mmole) 6,7,12,13-tetrahydro-3-methoxy-5,7-dioxo-5H-indolo[2,3-a]pyrrolo[3,4-c]carbazole and 2.0 g zinc amalgam are heated to a boil for one hour in 35 ml ethanol with vigorous stirring and with passing in of HCl gas. One allows to cool, rotary evaporates off the solvent and treats the residue five times with, in each case, 100 ml hot ethyl acetate. The combined ethyl acetate extracts are washed out with dilute aqueous sodium carbonate solution, dried over sodium sulfate, and evaporated. The residue is first treated with hot acetone, then with hot acetonitrile, and filtered off with suction.

One obtains an about 3:5 regioisomeric mixture of 6,7,12,13-tetrahydro-9-methoxy-5-oxo-5H-indolo[2,3a]-pyrrolo[3,4-c]carbazole and 6,7,12,13-tetrahydro-3-methoxy-5-oxo-5H-indol½,3-a]pyrrolo[2,3c]carbazole in the form of pale beige crystals of the melting point 313° C. Thin layer chromatography on silica gel 60 F$_{254}$, elution agent ethyl acetate, R$_f$=0.33.

The 6,7,12,13-tetrahydro-3-methoxy-5,7-dioxo-5H-indolo[2,3-a]pyrrolo[3,4-c]carbazole used as starting material is prepared as follows:

1.0 g (2.3 mmole) 3-(3-methoxy-6-nitrophenyl)-6(2-nitrophenyl)-phthalimide, 3.0 g (11.6 mmole) triphenyl phosphine and 50 ml collidine are heated under reflux for 30 hours. The collidine is distilled off in a vacuum at 0.1 Torr and the residue stirred up with 30 ml methanol and kept overnight in a refrigerator. The precipitate formed is filtered off with suction, the filtrate evaporated. The oily residue is taken up in a little chloroform and flash chromatographed on silica gel. It is first eluted with chloroform and then with methanol. One obtains a dark yellow product of the mp >330° C. (decomp.). Thin layer chromatography on silica gel 60 F$_{254}$, elution agent hexane/ethyl acetate 1:1, R$_f$=0.23.

The 3-(3-methoxy-6-nitrophenyl)-6-(2-nitrophenyl) phthalimide used as starting product is prepared as follows:

1.0 g (2.3 mmole) 3-(3-methoxy-6-nitrophenyl)-6-(2-nitrophenyl)-2a,3,6,6a-tetrahydrophthalimide and 2.2 g (9.8 mmole) 2,3-dichloro-5,6-dicyano-p-benzoquinone are heated under reflux for five hours in 25 ml tert.-butylbenzene. One allows to cool, filters off the precipitate with suction, and treats it for five minutes with about 20 ml methanol in an ultrasonic bath. After filtering off with suction, one obtains brownish crystals of the mp 280°–281° C.

The 2a,3,6,6a-tetrahydro-3-(3-methoxy-6-nitrophenyl)-6-(2-nitrophenyl)-phthalimide used as starting product is prepared as follows:

3.0 g (9.2 mmole) (E,E)-1-(3-methoxy-6-nitrophenyl)-4-(2-nitrophenyl)-1,3-butadiene and 1,0 g (10 mmole) maleinimide are heated to 145° C. with stirring for 24 hours in 30 ml toluene. One allows to cool, filters off the precipitate with suction, and treats it for five minutes in an ultrasonic bath with about 20 ml methylene chloride. One obtains a brownish product, mp 217°–218° C.

The (E,E)-1-(3-methoxy-6-nitrophenyl)-4-(2-nitrophenyl)-1,3-butadiene used as starting product is prepared as follows:

21.5 g (42.3 mmole) 3-methoxy-6-nitrobenzyltriphenylphosphonium bromide and 2.5 g 18-crown-6 are dissolved in 350 ml dry methylene chloride and cooled under nitrogen to 0° C. Within 30 minutes one mixes portionwise with 5.8 g (42.3 mmole) dry, finely pulverized potassium carbonate and thereafter stirs for 30 minutes at 0° C. The reaction mixture changes color from ochre yellow to deep violet. One adds 7.1 g (40.2 mmole) o-nitrocinnamaldehyde thereto and further stirs for 2.5 days under nitrogen at room temperature. The reaction mixture is well washed out with 200 ml water and the organic phase dried over sodium sulfate. After drying, the methylene chloride is rotary evaporated off and the dark residue treated with a little toluene in an ultrasonic bath. The precipitate is filtered off with suction and the filtrate discarded. The precipitate is again first treated with a little methanol and then again with toluene in an ultrasonic bath. After filtering off with suction, one obtains pure E,E-diene of the mp 162°–163° C. In the toluene filtrate is present a mixture of E,Z- and E,E-diene. Addition of three drops of a saturated iodine solution in toluene and stirring overnight at room temperature leads to the formation of the E,E-product.

The 3-methoxy-6-nitrobenzyl triphenylphosphonium bromide used as starting product is prepared as follows:

A suspension of 11.6 g (65 mmole) N-bromosuccinimide and 10.9 g (65 mmole) 3-methyl-4-nitroanisole in 80 ml carbon tetrachloride is heated under reflux for about four hours. The reaction mixture is hereby irradiated with a 500-watt photolamp and every 30 minutes mixed, in each case, with 0.1 g dibenzoyl peroxide. After cooling, the dark reaction mixture is filtered and the filtrate evaporated. The oily residue is dissolved in 150 ml dry dimethylformamide and, after the addition of 15.3 g (58.4 mmole) triphenyl phosphine, heated to 100° C. for four hours. After cooling, the solvent is stripped off in a vacuum and the oily residue triturated with a little acetone. The yellowish precipitate obtained is filtered off with suction, washed out with a little cold acetone, and dried in the air, mp 230°-233° C.

The following compounds are obtained as regioisomeric mixture in an analogous manner.

2-Chloro-6,7,12,13-tetrahydro-5-oxo-5H-indolo[2,3-a]pyrrolo[3,4-c]carbazole and 10-chloro-6,7,12,13-tetrahydro-5-oxo-5H-indolo[2,3-a]pyrrolo[3,4-c]carbazole (2.a), mp >300° C. (decomp.) from methanol.

EXAMPLE 3

(according to process C)

2 (and 10)-Chloro-12-ethyl-6,7,12,13-tetrahydro-5-oxo-5H-indolo[2,3-a]pyrrolo[3,4-c]carbazole (3.a) and 2 and 10)-chloro-12,13-diethyl-6,7,12,13-tetrahydro-5-oxo-5H-indolo[2,3 -a]-pyrrolo[3,4-c]carbazole (3.b) and 2 (and 10)-chloro-13-ethyl-6,7,12,13-tetrahydro-5-oxo-5H-indolo[2,3-a]pyrrolo[3,4-c]carbazole (3.c).

Under nitrogen, one mixes a suspension of 13.3 g (0.44 mole) sodium hydride (80% in paraffin oil) in 15 ml dry dimethylformamide portionwise with 75 mg (0.21 mmole) 2 (and 10)-chloro-6,7,12,13-tetrahydro-5-oxo-5H-indolo[2,3-a]pyrrolo[3,4-c]carbazole (Example 2.a) and stirs for 30 minutes at room temperature. Thereafter, one adds dropwise thereto a solution of 40.4 mg (0.37 mmole) ethyl bromide in 1 ml dimethylformamide and further stirs for 20 hours at room temperature. The dimethylformamide is rotary evaporated off and the residue flash chromatographed on silica gel 60. As elution agent there serves a mixture of chloroform/methanol 30:1.

As first eluted product, one obtains 2 (and 10)-chloro-12,13-diethyl-6,7,12,13-tetrahydro-5-oxo-5H-indolo[2,3-a]pyrrolo[3,4-c]carbazole in the form of bright yellow crystals, mp 263° C. Thin layer chromatography on silica gel 60 F$_{254}$, elution agent toluene/ethanol 10:2, R$_f$ 0.50.

As second product is eluted 2 (and 10)-chloro-13-ethyl-6,7,12,13-tetrahydro-5-oxo-5H-indolo[2,3-a]-pyrrolo[3,4-c]carbazole. It forms dark yellow crystals, mp >360° C. Thin layer chromatography on silica gel 60 F$_{254}$, elution agent toluene/ethanol 10:2, R$_f$ 0.45.

As finally eluted product there is obtained 2 (and 10)-chloro-12-ethyl-6,7,12,13-tetrahydro-5-oxo-5H-indolo[2,3-a]pyrrolo[3,4-c]carbazole in the form of beige crystals, mp 245° C. (decomp.). Thin layer chromatography on silica gel 60, elution agent toluene/ethanol 10:2, R$_f$ 0.43.

EXAMPLE 4

(according to process C)

12-Ethyl-6,7,12,13-tetrahydro-3,9-dimethoxy-5-oxo-5H-indolo[2,3-a]pyrrolo[3,4-c]carbazole and
13-ethyl-6,7,12,13-tetrahydro-3,9-dimethoxy-5-oxo-5H-indolo-[2,3-a]pyrrolo[3,4-c]carbazole.

15 mg (0.50 mmole) sodium hydride (80% in mineral oil) are suspended in 20 ml dry dimethylformamide and 150 mg (0.40 mmole) 6,7,12,13-tetrahydro-3,9-dimethoxy-5-oxo-5H-indolo[2,3-a]pyrrolo[3,4-c]carbazole (Example 1.a) added portionwise thereto at room temperature. After subsidence of the gas evolution, it is after stirred for one hour at room temperature, then 75 mg (0.48 mmole) ethyl iodide added thereto and stirred at room temperature for 16 hours. The solvent is distilled off in a vacuum and the residue chromatographed on silica gel with dichloromethane/methanol 95:5. The fraction with the R$_f$ of 0.3 is isolated, stirred with diisopropyl ether/ethyl acetate and the crystals formed filtered off.

One obtains an about 3:1 regioisomeric mixture of 12-ethyl-6,7,12,13-tetrahydro-3,9-dimethoxy-5-oxo-5H-indolo[ 2,3-a]pyrrolo[3,4-c]carbazole and 13-ethyl-6,7,12,13-tetrahydro-3,9-dimethoxy-5-oxo-5H-indolo-[2,3-a]pyrrolo[3,4-c]carbazole in the form of beige crystals which decompose above 280° C.

In analogous manner is obtained:
12-methyl-6,7,12,13-tetrahydro-3,9-dimethyl-5oxo-5H-indolo[2,3-a]pyrrolo[3,4-c]carbazole and 13-methyl-6,7,12,13-tetrahydro-3,9-dimethyl-5-oxoindolo[2,3-a]pyrrolo[3,4-c]carbazole (4.a), mp >340° C. from diisopropyl ether/ethyl acetate; 93:7 - mixture of regioisomers.

EXAMPLE 5

(according to process C)

12,13-Diethyl-6,7,12,13-tetrahydro-3,9-dimethoxy-5-oxo-5H-indolo-[2,3-a]pyrrolo[3,4-c]carbazole.

The crude product obtained by reaction analogously to Example 4 of 150 mg (0.40 mmole) 6,7,12,13-tetrahydro-3,9-dimethoxy-5-oxo-5H-indolo[2,3-a]pyrrolo[3,4-c]carbazole (Example 1.a) with 30 mg (1 mmole) sodium hydride (80% in mineral oil) and 150 ml (0.96 mmole) ethyl iodide is separated chromatographically on silica gel with dichloromethane/methanol 95:5. The fraction with the R$_f$ of 0.35 is isolated, stirred with diisopropyl ether/ethyl acetate, and the crystals formed filtered off. One obtains 12,13-diethyl-6,7,12,13-tetrahydro-3,9-dimethoxy-5-oxo-5H-indolo[2,3-a]pyrrolo[3,4-c]carbazole in the form of beige crystals of the mp 193°-196° C.

In an analogous manner are obtained:
12,13-Dimethyl-6,7,12,13-tetrahydro-3,9-dimethyl-5-oxo-5H-indolo[2,3-a]pyrrolo[3,4-c]carbazole (5.a), mp >280° C. (decomp.) from diisopropyl ether/ethyl acetate, 12,13-Dimethyl-6,7,12,13-tetrahydro-3,9-dimethoxy-5-oxo-5H-indolo[2,3-a]pyrrolo[3,4-c]carbazole (5.b).

EXAMPLE 6

6,7,12,13-Tetrahydro-3,9-dihydroxy-5-oxo-5H-indolo-[2,3-a]pyrrolo[3,4-c]carbazole.

To 250 mg (0.67 mmole) 6,7,12,13-tetrahydro-3,9-dimethoxy-5-oxo-5H-indolo[2,3 -a]pyrrolo[3,4-c]carbazole (Example 1.a) in 10 1 trockenem dichloromethane a solution of 506 mg (2 mmole) boron tribromide in 5 ml dichloromethane is added at −10° C. The mixture is stirred one hour at −10° C., thereafter two hours at 20° C. Subsequently, 50 ml of water is added dropwise under cooling with ice, and the mixture is extracted with ethyl acetate (300 ml). The unsolved crude product is filtered off and is separated chromatographically together with the crude product, obtained by evaporating the organic phase, on silica gel with dichloromethane/methanol 9:1. The fraction with R$_f$ 0.1 is isolated, stirred up with diisopropyl ether/methanol, and the crystals formed are filtered off.

One obtains 6,7,12,13 -tetrahydro-3,9-dihydroxy-5-oxo-5H-indolo[2,3-a]pyrrolo[3,4-c]carbazole in the form of beige crystals, mp >330° C.

EXAMPLE 7

6,7,12,13-Tetrahydro-5-Oxo-12,13-dipropyl-5H-indolo-[2,3-a]pyrrolo[3,4-.c]carbazole.

20 mg (0.67 mmole) sodium hydride (80% in mineral oil) is suspended in 10 ml dry dimethylformamide and 100 mg (0.32 mole) 6,7,12,13-tetrahydro-5c-oxo-5H-indolo[2,3-a]pyrrolo[3,4-c]carbazole are added portionwise thereto at ambient temperature. After subsidence of the gas evolution, the reaction mixture is further stirred for one hour at ambient temperature and then 120 mg (0.71 mmole) n-propyl iodide are added thereto and stirring continued for 16 hours at ambient temperature. The solvent is removed by rotary evaporation in a vacuum and the residue is chromatographed on silica gel with toluene/ethyl acetate (1:1 v/v). The fraction with the $R_f$ of 0.4 is isolated and stirred with diisopropyl ether. The crystals formed are filtered off with suction. 6,7,12,13-Tetrahydro-5-oxo-12,13 -dipropyl-5H-indolo[2,3-a]pyrrolo[3,4-c]carbazole is obtained in the form of beige crystals; mp 180°–185° C. (decomp.), yield 43%.

In an analogous manner, there is obtained 12,13-diethyl-6,7,12,13-tetrahydro-5-oxo-5H-indolo-[2,3-a]pyrrolo[3,4-c]carbazole (1.a) ;mp >225° C. (decomp.), after crystallization from diisopropyl ether, yield 32%.

With the use of two equivalents of sodium hydride and one equivalent of 1,4-dibromobutane, there is obtained, in an analogous manner, 12,13-butano-6,7,12,13-tetrahydro-5-oxo-5H-indolo]2,3-a]pyrrolo-[ 3,4-c]carbazole (1.b); mp >300° C., after crystallization from diisopropyl ether, yield 53%.

In an analogous manner, there is obtained 12,13-dibenzyl-6,7,12,13-tetrahydro-5-oxo-5H-indolo-[2,3-a]pyrrolo[3,4-c]carbazole (1.c), mp >250° C. (decomp.) from diisopropyl ether, yield 33%; 12,13-dioctadecyl-6,7,12,13-tetrahydro-5-oxo-5H-indolo[2,3-a]pyrrolo[3,4-c]carbazole (1.d), mp 101°–103° C. from diisopropyl ether/ethylacetate, yield 42%.

EXAMPLE 8

6,7,12,13-Tetrahydro-5-oxo-12-propyl-5H-indolo [2,3 -a]-pyrrolo[3,4-c]carbazole and
6,7,12,13-tetrahydro-5-oxo-13-propyl-5H-indol[2,3-a]-pyrrolo[3,4-c]carbazole.

The crude product obtained by the reaction of 100 mg (0.32 mmole) 6,7,12,13-tetrahydro-5-oxo-5H-indol[2,3-a]pyrrolo[3,4-c]carbazole with 10 mg (0.33 mmole) sodium hydride (80% in mineral oil) and 60 mg (0.35 mmole) n-propyl iodide analogously to Example 1 is separated chromatographically on silica gel with toluene/ethyl acetate (1:1 v/v). The fraction with the $R_f$ of 0.3 is isolated and stirred with diisopropyl ether. The beige crystals formed are filtered off.

There is obtained an approximately 3:1 regioisomeric mixture of 6,7,12,13-tetrahydro-5-oxo-12-propyl-5H-indolo[2,3-a]pyrrolo[3,4-c]carbazole and 6,7,12,13-tetrahydro-5-oxo-13-propyl-5H-indolo-[2,3-a]-pyrrolo[3,4-c]carbazole; mp about 300° C. (decomp.), yield 44%.

In an analogous manner, there is obtained:
6,7,12,13-tetrahydro-12-(2-methoxyethyl)-5-oxo-5H-indolo [2,3 -a]pyrrolo [3,4 -c]carbazole and 6,7,12,13-tetrahydro-13-(2-methoxyethyl)-5-oxo-5H-indolo[2,3 -a]pyrrolo[3,4-c]carbazole (2.a), mp >250° C. (decomp.) from diisopropyl ether, in a 5:1 regioisomeric mixture, yield 26%.

With one equivalent sodium hydride and one equivalent acetic anhydride and chromatographic separation of the regioisomers there is obtained: 13-acetyl-6,7,12,13-tetrahydro-5-oxo-5H-indolo[2,3-a]-pyrrolo[3,4-c]carbazole (2.b), mp >315° C. (decomp.) from diisopropyl ether, yield 14%; 6,7,12,13-tetrahydro-12-octadecyl-5-oxo-5H-indolo-[2,3-a]pyrrolo[3,4-c]carbazole and 6,7,12,13-tetrahydro-13-octadecyl-5-oxo-5H-indolo[2,3-a]pyrrolo-[3,4-c]carbazole (2.c), mp 170°–185° C. from diisopropyl ether/ethylacetate, 2:1 regioisomeric mixture, yield 40%.

EXAMPLE 9

12-Ethyl-6,7,12,13-tetrahydro-5-oxo-5H-indolo]2,3-a]-pyrrolo[3,4-c]carbazole

The crude product obtained by the reaction of 200 mg (0.64 mmole) 6,7,12,13-tetrahydro-5-oxo-5H-indolo[2,3-.a]pyrrolo[3,4-c]carbazole with 20 mg (0.66 mmole) sodium hydride (80% in mineral oil) and 110 mg (0.71 mmole) ethyl iodide analogously to Example 1 is separated chromatographically on silica gel with toluene/ethyl acetate (1:1 v/v). The fraction with the $R_f$ of 0.25 is isolated, stirred with toluene/ethanol (9:1 v/v) and the crystals formed are filtered off. The approximately 3:1 regioisomeric mixture obtained of 12-ethyl- 6,7,12,13-tetrahydro-5-oxo-5H-indolo]2,3-a]pyrrolo[3,4-c]carbazole and 13-ethyl-6,7,12,13-tetrahydro-5-oxo-5H-indolo]2,3-a]pyrrolo[3,4-c]carbazole is boiled up with acetone and the crystals are filtered off after cooling.

There is obtained 12-ethyl-6,7,12,13 -tetrahydro-5-oxo-5H-indolo[2,3-a]pyrrolo[3,4-c]carbazole in the form of beige crystals; mp >290° C. (decomp.), yield 27%.

EXAMPLE 10

12-(3-Dimethylaminopropyl)-6,7,12,13-tetrahydro-5-oxo-5H-indolo[2,3-a]pyrrolo[3,4-c]carbazole and 13-(3 -dimethylaminopropyl)-6,7,12,13-tetrahydro-5-oxo-5H-indolo[2,3-a]pyrrolo[3,4-c]carbazole.

The crude product obtained by the reaction of 150 mg (0.48 mmole) 6,7,12,13-tetrahydro-5-oxo-5H-indolo[2,3-a]pyrrolo[3,4-c]carbazole with 18 mg (0.60 mmole) sodium hydride (80% in mineral oil) and 73 mg (0.60 mmole) 3-dimethylaminopropyl chloride analogously to Example 1 is separated chromatographically on silica gel with ethyl acetate/acetone (1:1 v/v). The fraction with the $R_f$ of 0.1 is isolated and stirred with diisopropyl ether. The crystals formed are filtered off.

There is obtained approximately 6:1 regioisomeric mixture of 12-(3-dimethylaminopropyl)-6,7,12,13-tetrahydro-5-oxo-5H-indolo[2,3-a]pyrrolo[3,4-c]-carbazole and 13-(3-dimethylaminopropyl)-6,7,12,13-tetrahydro-5-oxo-5H-indolo[2,3-a]pyrrolo[3,4-c]-carbazole in the form of beige crystals; mp 265° C. (decomp.), yield 48%.

There is obtained in analogous manner:
6,7,12,13-tetrahydro-12-(2-morpholinoethyl)-5-oxo-5H-indolo [2,3-a]pyrrolo[3,4-c]) carbazole and 6,7,12,13-tetrahydro-13-(2-morpholinoethyl)-5-oxo-5H-indolo-2,3-a]pyrrolo[3,4-c]carbazole (4.a), mp >230° C. (decomp.) from diisopropyl ether, 3:1 regioisomeric mixture, yield 30%;
6,7,12,13-tetrahydro-5-oxo-12-(2-pyrrolidinoethyl)-5H-indolo[2,3-a]pyrrolo[3,4-c]carbazole and 6,7,12,13-tetrahydro-5-oxo-13-(2-pyrrolidinoethyl)-5H-indolo-[2,3-a]pyrrolo[3,4-c]carbazole (4.b), mp 239°–243° C. from diisopropyl ether-/ethylacetate, yield 28%;

(+)-12-(3-diethylamino-2-methoxy-1-propyl)-6,7,12,13-tetrahydro-5-oxo-5H-indolo[2,3-a]pyrrolo[3,4-c]carbazole and (+)-13-(3-diethylamino-2-methoxy-1-propyl)-6,7,12,13-tetrahydro-5-oxo-5H-indolo-[2,3 -a] pyrrolo[3,4-c]carbazole (4.c), mp 240°–260° C. (decomp.) from diisopropyl ether-/ethylacetate, 3:1 regioisomeric mixture, yield 54%;

(+)-12-(3-dimethylamino-2-methoxy-1-propyl)-6,7,12,13-tetrahydro-5-oxo-5H-indolo[2,3-a]pyrrolo[3,4-c]carbazole and (+)-13-(3-dimethylamino-2-methoxy-1-propyl)-6,7,12,13-tetrahydro-5-oxo-5H-indolo[2,3-a]-pyrrolo[3,4-c]carbazole (4.d), mp >190° C. (decomp.) from diisopropyl ether/ethylacetate, 7:3 regioisomeric mixture, yield 21%;

(+)-12-[3-(N-benzyl-N-methylamino)-2-methoxy-1-propyl]-6,7,12,13-tetrahydro-5-oxo-5H-indolo[2,3-a]-pyrrolo [3,4-c]carbazole and (+)-13-[3-N-benzyl-N-methylamino)-2-methoxy-1-propyl]-6,7,12,13-tetrahydro-5-oxo-5H-indolo[2,3-a]pyrrolo[3,4-c]carbazole (4.e), mp >150° C. (decomp.) from diisopropyl ether/ethylacetate, 5:3 regioisomeric mixture, yield 32%;

6,7,12,13-tetrahydro-5-oxo-12-(3-piperidinopropyl)-5H-indolo-[2,3-a]pyrrolo[3,4-c]carbazole and 6,7,12,13-tetrahydro-5-oxo-13-(3-piperidinopropyl)-5H-indolo-[2,3-a]pyrrolo[3,4-c]carbazole (4.f), mp >230° C. (decomp.) from diisopropyl ether, 7:4 regioisomeric mixture, yield 17%.

EXAMPLE 11

6,7,12,13-Tetrahydro-12-methyl-5-oxo-5H-indolo [2,3-a]-pyrrolo[3,4-c]carbazole and 6,7,12,13 -tetrahydro-13-methyl-5-oxo-5H-indolo[2,3-a]-pyrrolo[3,4-c]carbazole.

29 mg (0.97 mmole) sodium hydride (80% in mineral oil) is suspended in 20 ml dry dimethylformamide and 200 mg (0.64 mmole) 6,7,12,13-tetrahydro-5-oxo-5H-indolo[2,3-a]pyrrolo[3,4-c]carbazole added portionwise thereto at ambient temperature. After subsidence of the gas evolution, 0.09 ml (0.95 mmole) dimethyl sulfate is added thereto and the reaction mixture is stirred for 72 hours at ambient temperature. The solvent is distilled of in a vacuum and the residue mixed with 20 ml aqueous sodium carbonate solution. It is extracted twice with, in each case, 20 ml ethyl acetate. The ethyl acetate solutions are dried over anhydrous sodium sulfate and subsequently evaporated in a vacuum. The residue is chromatographed on silica gel with dichloromethane/methanol (95:5 v/v). The fraction with the $R_f$ of 0.4 is isolated and stirred with diisopropyl ether/acetone (9:1 v/v). The crystals formed are filtered off.

There is obtained an approximately 7:1 regioisomeric mixture of 6,7,12,13-tetrahydro-12-methyl-5-oxo-5H-indolo[2,3-a]pyrrolo[3,4-c]carbazole and 6,7,12,13-tetrahydro-13-methyl-5-oxo-5H-indolo]-2,3-a]pyrrolo[3,4-c]carbazole in the form of beige crystals; mp >300° C. (decomp.), yield 38%.

With two equivalents of sodium hydride and dimethyl sulfate, there is obtained, in an analogous way, 6,7,12,13-tetrahydro-12,13-dimethyl-5-oxo-5H-indolo-[2,3-a]pyrrolo[3,4-v]carbazole (5.1); mp 248°–251° C., after crystallization from diisopropyl ether, yield 56%.

EXAMPLE 12

6,7,12,13-Tetrahydro-7-hydroxy-5-oxo-5H-indolo [2,3-a]pyrrolo[3,4-c]carbazole (6.1) and 7-ethoxy-6,7,12,13-tetrahydro-5-oxo-5H-indolo[2,3-a]pyrrolo [3,4-c]carbazole (6.b).

To a stirred suspension of 10 g (153 mmole) zinc dust and 1 g (3.7 mmole) mercuric chloride in 10 ml water is added 0.5 ml concentrated hydrochloric acid. After about five minutes, the supernatant liquid is decanted off. The zinc amalgam thus obtained is first washed with water and subsequently repeatedly washed with ethanol. After the addition of 30 ml dry ethanol, the mixture is cooled in an ice bath and 300 mg (1.01 mmole) 6,7,12,13-tetrahydro-5,7-dioxo-5H-indolo[2,3-a]pyrrolo[3,4-c]carbazole are added thereto. Dry gaseous hydrogen chloride is then slowly passed in over the course of one hour, with further cooling. The reaction mixture is filtered, the filtrate is evaporated and the residue is chromatographed on silica gel with toluene-/ethyl acetate (1:1 v/v). The fraction with the $R_f$ of 0.3 is isolated and crystallized from ethyl acetate.

There are obtained beige crystals of 7-ethoxy-6,7,12,13 -tetrahydro-5-oxo-5H-indolo[2,3-a]pyrrolo[3,4-c]carbazole (6.b); mp >300° C., yield 22%.

The fraction with the $R_f$ of 0.2 is isolated and stirred with diisopropyl ether. There are obtained beige crystals of 6,7,12,13 -tetrahydro-7-hydroxy-5-oxo-5H-indolo[2,3-a]pyrrolo[3,4-c]carbazole (6.a); mp >300° C., yield 23%.

EXAMPLE 13

6,7,12,13-Tetrahydro-12-methoxycarbonylmethyl-5-oxo-5H-indolo[2,3-a]pyrrolo[3,4-c]carbazole and 6,7,12,13-tetrahydro-13-methoxycarbonylmethyl-5-oxo-5H-indolo-[2,3-a]pyrrolo[3,4-c]carbazole.

The crude product obtained by the reaction of 150 mg (0.48 mmole) 6,7,12,13-tetrahydro-5-oxo-5H-indolo [2,3 -a]pyrrolo[3,4-c]carbazole with 18 mg (0.60 mmole) sodium hydride (80% in mineral oil) and 115 mg (0.75 mmole) methyl bromoacetate analogously to Example 1 is separated chromatographically on silica gel with dichloromethane/methanol (95:5 v/v). The fraction with the $R_f$ of 0.35 is isolated and stirred with diisopropyl ether. The crystals formed are filtered off.

There is obtained an approximately 3:1 regioisomeric mixture of 6,7,12,13-tetrahydro-12-methoxycarbonyl-methyl-5-oxo-5H-indolo[2,3-a]pyrrolo[3,4-c]-carbazole and 6,7,12,13-tetrahydro-13-methoxycarbonylmethyl-5-oxo-5H-indolo[2,3-a]pyrrolo[3,4-c]carbazole in the form of beige crystals; mp >300° C., yield 51%.

EXAMPLE 14

(+)-6,7,12,13-Tetrahydro-12,13-(2-hydropropano)-5-oxo-5H-indolo[2,3-a]pyrrolo[3,4- c]carbazole.

The crude product obtained by the reaction of 300 mg (0.96 mmol) 6,7,12,13-tetrahydro-5-oxo-5H-indolo-[2,3-a]pyrrolo[3,4-c]carbazole with 33 mg (1.1 mmol) sodium hydride (80% in mineral oil) and 0.1 ml (1.2 mmol) epibromhydrine in 30 ml dry dimethylformamide analogously to Example 1 (reaction time 72 hours at ambient temperature) is separated chromatographically on silica gel with cyclohexane/tetrahydrofuran (1:1 v/v). The fraction with the $R_f$ of 0.15 in toluene/ethylacetate (1:1 v/v) is isolated and stirred with diisopropyl ether/methanol. The crystals formed are filtered off.

There is obtained 6,7,12,13-tetrahydro-12,13-(2-hydroxypropano)-5-oxo-5H-indolo[2,3-a]pyrrolo[3,4-c]carbazole in the form of beige crystals; mp >300° C. (decomp.), yield 19%.

EXAMPLE 15

(+)-12-(3-Diethylamino-2-hydroxy-1-propyl)-6,7,12,13-tetrahydro-5-oxo-5H-indolo[2,3-a]pyrrolo[3,4-c]carbazole and
(+)-13-(3-diethylamino-2-hydroxy-1-propyl)-6,7,12,13-tetrahydro-5-oxo-5H-indolo [2,3-a]pyrrolo[3,4-c]carbazole.

The crude product obtained by the reaction of 500 mg (1.61 mmole) 6,7,12,13-tetrahydro-5-oxo-5H-indolo[2,3-a]pyrrolo[3,4-c]carbazole with 58 mg (1.92 mmole) sodium hydride (80% in mineral oil) and 447 mg (2.70 mmole) 1,1-diethyl-3-hydroxyazetidinium-chloride in 50 ml dry dimethylformamide analogously to Example 1 is extracted with 200 ml ethylacetate and 50 ml water. The organic phase is separated, dried with sodium sulfate and evaporated. The residue is separated chromatographically on silica gel with dichloromethane/methanol (95:5 v/v). The fraction with the R$_f$ of 0.1 is isolated and stirred with diisopropyl ether/ethylacetate. The crystals formed are filtered off.

There is obtained an approximately 1:1 regioisomeric mixture of (±)-12-(3-diethylamino-2-hydroxylpropyl)-6,7,12,13-tetrahydro-5-oxo-5H-indolo[2,3-a]pyrrolo[3,4-c]carbazole and (±)-13-(3-diethylamino-2-hydroxy-1-propyl)-6,7,12,13-tetrahydro-5-oxo-5H-indolo[2,3-a]pyrrolo[3,4-c]carbazole in the form of pale beige crystals; mp >195° C. (decomp.), yield 44%.

There is obtained in an analogous manner:

(+)12-(3-piperidino-2-hydroxy-1-propyl)-6,7,12,13-tetrahydro-5-oxo-5H-indolo[2,3-a]pyrrolo[3,4-c]carbazole and (±)-13-(3-piperidino-2-hydroxy-1-propyl)-6,7,12,13-tetrahydro-5-oxo-5H-indolo[2,3-a]pyrrolo-3,4-c]carbazole (9.a), mp >205° C. (decomp.) from diisopropyl ether, yield 28%.

EXAMPLE 16

(±)-6,7,12,13-Tetrahydro-12-(3-N-methylamino-2-methoxy-1-propyl)-5-oxo-5H-indolo[2,3-a]pyrrolo[3,4-c] carbazole and
(+)-6,7,12,13-tetrahydro-13-(3-N-methylamino-2-methoxy-1-propyl)-5-oxo-5H-indolo[2,3-a]pyrrolo[3,4-c]carbazole.

100 mg (0.2 mmol) (±)-12-[3-(N-benzyl-N-methylamino)-2-methoxy-1-propyl]-6,7,12,13-tetrahydro-5-oxo-5H-indolo[2,3-a]pyrrolo[3,4-c]carbazole and (±)-13-[3-(N-benzyl-N-methylamino)-2-methoxy-1-propyl]-6,7,12,13-tetrahydro-5-oxo-5H-indolo[2,3-a]pyrrolo[3,4c]carbazole (Example 4.e) in 30 ml glacial acetic acid are hydrogenated five hours with 100 mg Palladium on charcoal (10% Pd/50% water) at 55°-60° C. The catalyst will be filtered off, the solution evaporated, and the residue partitioned between sodium hydrogen carbonate solution (50 ml) and ethyl acetate (100 ml). The organic phase is separated off, dried over sodium sulfate, and evaporated. The residue is stirred with diisopropyl ether/ethylacetate (4:1, v:v), the crystals filtered off and dried.

One obtains (±)-6,7,12,13-tetrahydro-12-(3-N-methylamino-2-methoxy-1-propyl)-5-oxo-5H-indolo[2,3-a]pyrrolo[3,4-c]carbazole and (±)-6,7,12,13-tetrahydro-13-(3-N-methylamino-2-methoxy-1-propyl)-5-oxo-5H-indolo[2,3-a]pyrrolo[3,4-c]carbazole in the form of pale beige crystals of the mp >170° C. (decomp.), yield 62%, as 3:1 regioisomeric mixture.

What is claimed is:

1. A compound of the formula or a pharmaceutically acceptable salt thereof wherein $R^1$ and $R^2$ taken together are alkylene of from 2–4 carbon atoms unsubstituted or substituted by hydroxyl, alkoxy of 1–4 carbon atoms or amino which is unsubstituted or is mono- or di-substituted by benzyl or by alkyl of from 1–4 carbon atoms;

X and Y are each hydrogen or one is hydrogen and the other is hydroxyl or alkoxy of from 1–4 carbon atoms;

$R^3$, $R^4$, $R^5$, $R^6$, and $R^{10}$ are each independently
hydrogen,
bromine,
chlorine,
methyl,
ethyl,
hydroxyl
methoxy,
2-aminoethoxy,
3-aminopropoxy,
1-amino-2-propoxy,
2-dimethylaminoethoxy,
3-dimethylamino-1-propoxy,
3-dimethylamino-2-propoxy, or
2-diethylaminoethoxy;

$R^6$ and $R^7$ are hydrogen with the proviso that at least one and as many as four of $R^3$ to $R^4$ are not hydrogen.

2. A compound described as 12, 13-butano-6,7,12,13-tetrahydro-5-oxo-5H-indolo [2,3-a]pyrrolo [3,4-c]carbazole.

3. The compound of the formula or a pharmaceutically acceptable salt thereof wherein $R^1$ and $R^2$ taken together are alkylene of from 2–4 carbon atoms unsubstituted or substituted by hydroxyl, alkoxy of 1–4 carbon atoms or amino which is unsubstituted or is mono- or di-substituted by benzyl or by alkyl of from 1–4 carbon atoms;

X and Y are each hydrogen or one is hydrogen and the other is hydroxyl or alkoxy of from 1–4 carbon atoms;

$R^3$, $R^4$, $R^5$, $R^6$, $R^9$ and $R^{10}$ are each independently hydrogen, bromine, chlorine, alkyl of from 1–4 carbon atoms or alkoxy of from 1–4 carbon atoms;

$R^6$ and $R^7$ are hydrogen with the proviso that at least one and as many as four of $R^3$ to $R^{10}$ are not hydrogen.

4. A pharmaceutical composition for treating blood vessel diseases comprising an effective amount of a compound according to claim 1 in admixture with a pharmaceutically acceptable carrier.

5. A method for treating diseases of blood vessels which comprises treating a host suffering therefrom with a pharmaceutical composition according to claim 1 in unit dosage form.

6. A compound according to claim 1 wherein $R^5$ or $R^8$ is methoxy, methyl, or chloro.

7. A compound according to claim 1 wherein $R^4$ or $R^9$ is methoxy, methyl, or chloro.

8. A compound according to claim 1 wherein $R^5$ and $R^8$ are both methoxy, hydroxyl, methyl, bromo, or chloro.

9. A compound according to claim 1 wherein $R^4$ and $R^9$ are both methoxy, methyl, bromo, or chloro.

10. A compound according to claim 1 wherein $R^4$ and $R^5$ or $R^8$ and $R^9$ are the same and are methoxy.

11. A compound according to claim 1 wherein $R^4$, $R^5$, $R^8$, and $R^9$ are methoxy and $R^3$, $R^6$, $R^7$ and $R^{10}$ are hydrogen.

12. A pharmaceutical composition comprising an effective amount of a compound as defined in claim 1 in combination with a pharmaceutically acceptable carrier.

13. A method for treating and/or preventing heart and blood vessel diseases which comprises administering to a mammal in need of such treatment a composition according to claim 12 in unit dosage form.

14. A compound according to claim 1 wherein $R_1$ and $R_2$ when taken together form a butylene or a propylene radical unsubstituted or hydroxy substituted.

* * * * *

UNITED STATES PATENT AND TRADEMARK OFFICE
CERTIFICATE OF CORRECTION

PATENT NO. : 5,438,050
DATED : August 1, 1995
INVENTOR(S) : Kleinschroth et al.

It is certified that error appears in the above-indentified patent and that said Letters Patent is hereby corrected as shown below:

Column 26, line 27, delete " $R^6$, " and insert instead " $R^8$, $R^9$, " .

Column 26, line 44, delete " $R^4$ " and insert instead " $R^{10}$ " .

Column 27, line 4, delete " $R^6$, " and insert instead " $R^8$, " .

Signed and Sealed this

Thirteenth Day of February, 1996

Attest:

BRUCE LEHMAN

*Attesting Officer*   Commissioner of Patents and Trademarks